(12) United States Patent
Wang et al.

(10) Patent No.: US 10,689,341 B2
(45) Date of Patent: Jun. 23, 2020

(54) SMALL MOLECULE N-(ALPHA-PEROXY) INDOLE COMPOUNDS AND METHODS OF USE

(71) Applicant: King Abdullah University of Science and Technology, Thuwal (SA)

(72) Inventors: Xinbo Wang, Thuwal (XK); Zhiping Lai, Thuwal (SA); Yupeng Pan, Thuwal (SA); Kuowei Huang, Thuwal (SA); Zhigang Wang, Shenzhen (CN)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 16/099,853

(22) PCT Filed: May 10, 2017

(86) PCT No.: PCT/IB2017/052742
§ 371 (c)(1),
(2) Date: Nov. 8, 2018

(87) PCT Pub. No.: WO2017/195136
PCT Pub. Date: Nov. 16, 2017

(65) Prior Publication Data
US 2019/0112267 A1 Apr. 18, 2019

Related U.S. Application Data

(60) Provisional application No. 62/334,518, filed on May 11, 2016.

(51) Int. Cl.
| | | |
|---|---|---|
| C07D 209/08 | (2006.01) |
| C07D 209/16 | (2006.01) |
| C07D 209/24 | (2006.01) |
| C07D 209/48 | (2006.01) |
| A61K 31/404 | (2006.01) |
| A61K 31/4045 | (2006.01) |
| A61K 45/06 | (2006.01) |
| C07D 209/14 | (2006.01) |
| C07D 209/26 | (2006.01) |
| C07D 403/06 | (2006.01) |

(52) U.S. Cl.
CPC .......... *C07D 209/08* (2013.01); *A61K 31/404* (2013.01); *A61K 31/4045* (2013.01); *A61K 45/06* (2013.01); *C07D 209/14* (2013.01); *C07D 209/16* (2013.01); *C07D 209/24* (2013.01); *C07D 209/26* (2013.01); *C07D 209/48* (2013.01); *C07D 403/06* (2013.01)

(58) Field of Classification Search
CPC ........................... C07D 209/08; A01K 31/404
See application file for complete search history.

(56) References Cited

FOREIGN PATENT DOCUMENTS

CN 104610125 5/2015

OTHER PUBLICATIONS

Wang et al (2015), STN International (Columbus, Ohio) Hcaplus database, Accession No. 2015: 1830821.*
Search Report and Written Opinion for PCT/IB2017/052742 dated Jun. 3, 2017.
Wang, et al., "One-Pot Synthesis of N-([alpha]-Peroxy)Indole/Carbazole via Chemoselective Three-Component condensation Reaction in Open Atmosphere", Organic Letters • 14(23). 6012-6015 CODEN: ORLEF7; ISSN: 1523-7052, vol. 17, No. 22, Nov. 20, 2015 (Nov. 20, 2015), pp. 5630-5633.

* cited by examiner

*Primary Examiner* — Golam M Shameem
(74) *Attorney, Agent, or Firm* — Billion & Armitage; Lisbeth C. Robinson

(57) ABSTRACT

The invention relates to novel N-(α-peroxy)indole compounds of Formula I and methods for use. (I) The N-(α-peroxy)indole compounds described herein are useful for treating or preventing parasitic infections, bacterial infections, and cancer in subjects. The methods include administering an N-(α-peroxy)indole compound as described herein to a subject. Also described herein are methods for synthesizing N-(α-peroxy)indole compounds.

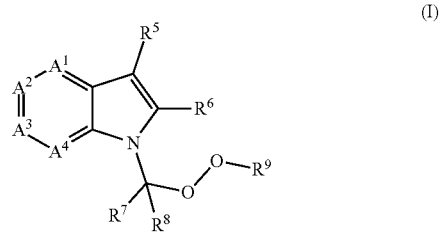

20 Claims, No Drawings

SMALL MOLECULE N-(ALPHA-PEROXY) INDOLE COMPOUNDS AND METHODS OF USE

RELATED APPLICATION DATA

This application claims the benefit of U.S. Provisional Patent Application Ser. No. 62/334,518, filed May 11, 2016.

TECHNICAL FIELD

The present invention relates to Small Molecule N-(Alpha-Peroxy) Indole Compounds and Methods of Use

BACKGROUND OF THE INVENTION

The background of this invention will address Malarial Infection, Resistance to Antimalarial Drugs and compounds.

Malarial Infection

Malaria is an infectious disease caused by mosquito-borne *Plasmodium* parasites affecting humans and other animals. The disease is prevalent in the tropical and subtropical regions of the world, particularly in areas around the equator. Malaria symptoms typically include chills, fever, fatigue, headaches, nausea or vomiting, and severe cases can result in seizures, coma, or death. More than 200 million cases of malaria occur worldwide annually resulting in over 500,000 deaths each year. The disease is most commonly transmitted by a bite from an infected Anopheles mosquito. The mosquito's saliva introduces the parasites into a person or animal's blood. Once in the bloodstream, the parasites travel to the liver where they mature and reproduce.

Malaria parasites belong to the genus *Plasmodium* (phylum Apicomplexa) and there are five known species of *Plasmodium* that can infect and be spread by humans. *Plasmodium falciparum* is the most common species identified in humans, followed by *P. vivax*. Less commonly isolated species are *P. malariae, P. ovale*, and *P. knowlesi*. *P. falciparum* generally accounts for the majority of deaths while *P. vivax, P. ovale*, and *P. malariae* usually causing a milder form of the disease.

Malaria infection develops via two phases: the first phase involves the liver, and the second phase involves the red blood cells. When an infected mosquito bites an individual, the *Plasmodium* sporozoites from the mosquito's saliva enter the bloodstream, and migrate to the liver. Once the sporozoites infect the liver cells, they multiply over a period of 8-30 days, eventually causing the infected liver cells to rupture. The parasites then return to the bloodstream, where they infect the red blood cells.

Because the malaria parasite resides for most of its human life cycle within the liver and blood cells, it is somewhat unnoticed by immune surveillance, and is consequently protected from the body's immune system. However, circulating infected blood cells are destroyed in the spleen. In addition to this, the *P. falciparum* parasite secrete adhesive proteins on the surface of the infected red blood cells, causing the blood cells to adhere to the walls of small blood vessels, further sequestering the parasite from the general circulation and the spleen.

Resistance to Antimalarial Drugs

As yet, there are no effective vaccines against malaria, and control of the disease depends upon antimalarial drugs that kill parasites inside the body. Diagnosis of malaria is made by microscopic examination of blood, or with antigen-based rapid diagnostic tests. Once diagnosed, the recommended treatment is a combination of antimalarial medications including chloroquine, quinine, mefloquine, amodiaquin, primaquine, pyrimethamine, sulfonamides, sulfones, dihydrofolate reductase inhibitors, and tetrandine, as well as others.

Recent decades have seen the emergence of parasites resistant to standard drug therapies, and drug resistance is increasingly a problem in malaria treatment. Antimalarial drugs, such as cryptolepine and artemisinin, are often initially effective; however, the parasites that cause the disease continuously evolve and become resistant to the drugs. Resistance is now common against most classes of antimalarial drugs. Treatment of resistant strains has become progressively more reliant on a few remaining drugs, and continued use of these drugs will increase the incidence of resistance. *P. falciparum* in particular has developed resistance to nearly all of the currently available antimalarial drugs.

Compounds

Furthermore, many effective antimalarial drugs include an organic peroxide moiety, which generally includes two carbon atoms linked by the peroxide bond atoms. The known methods for constructing the organic peroxide bond are highly inefficient and ineffective. For example, one method for constructing the organic peroxide moiety includes the coupling reaction of oxygen radicals to form a peroxide bond. The oxygen free radicals are highly reactive, which makes unwanted side reactions difficult to control.

The known methods for constructing the organic peroxide moiety require either a special substrate (e.g., benzylic amine with N protected) or special conditions (e.g., heavy metal or hv). Moreover, none of them can be integrated with the readily oxidizable indole residue and the classic peroxide oxidant to give N-(α-peroxy)indole, a somewhat rare structure that is present in active natural products.

SUMMARY OF THE INVENTION

The present invention is N-(α-peroxy)indole compounds and new methods of using and making the same are provided. A class of N-(α-peroxy)indole compounds as described herein includes compounds of the following formula:

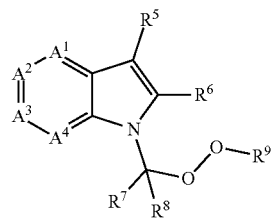

or a pharmaceutically acceptable salt or prodrug thereof, wherein $A^1$, $A^2$, $A^3$, and $A^4$ are each independently selected from CR and N, wherein each R is selected from the group consisting of hydrogen, halogen, cyano, trifluoromethyl, alkoxy, aryloxy, substituted or unsubstituted carbonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; $R^5$ and $R^6$ are each independently selected from hydrogen, halogen, cyano, trifluoromethyl, alkoxy, aryloxy, substituted or unsubstituted carbonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and $R^7$, $R^5$, and $R^9$ are each independently selected from hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl. In these compounds, $R^5$ and $R^6$ do not combine to form a cyclic compound.

Optionally, the compound has the following formula:

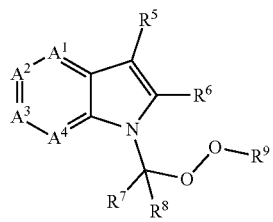

or a pharmaceutically acceptable salt or prodrug thereof, wherein $R^1$, $R^2$, $R^3$, $R^4$, $R^5$, and $R^6$ are each independently selected from hydrogen, halogen, cyano, trifluoromethyl, alkoxy, aryloxy, substituted or unsubstituted carbonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and $R^7$, $R^5$, and $R^9$ are each independently selected from hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl. Optionally, $R^1$ can be hydrogen. Optionally, $R^2$ can be hydrogen or alkoxy. $R^3$ and/or $R^4$ can optionally be hydrogen. $R^5$ can optionally be substituted or unsubstituted alkyl. $R^6$ can optionally be hydrogen. Optionally, $R^7$ can be substituted or unsubstituted alkyl or substituted or unsubstituted aryl. $R^8$ can optionally be hydrogen. $R^9$ can optionally be substituted or unsubstituted alkyl.

Optionally, the compound has the following formula:

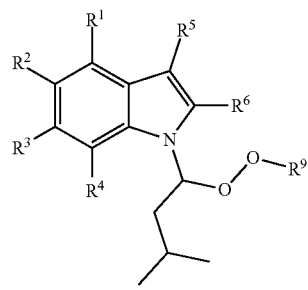

or a pharmaceutically acceptable salt or prodrug thereof. Optionally, the N-(α-peroxy)indole compound is a compound selected from the group consisting of:

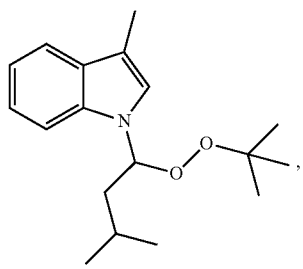

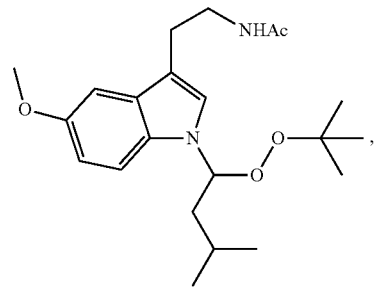

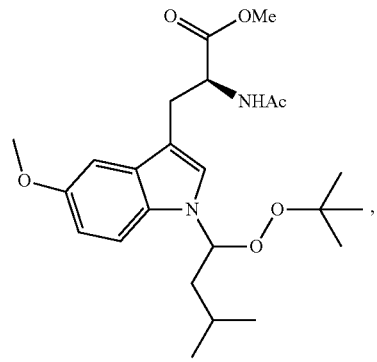

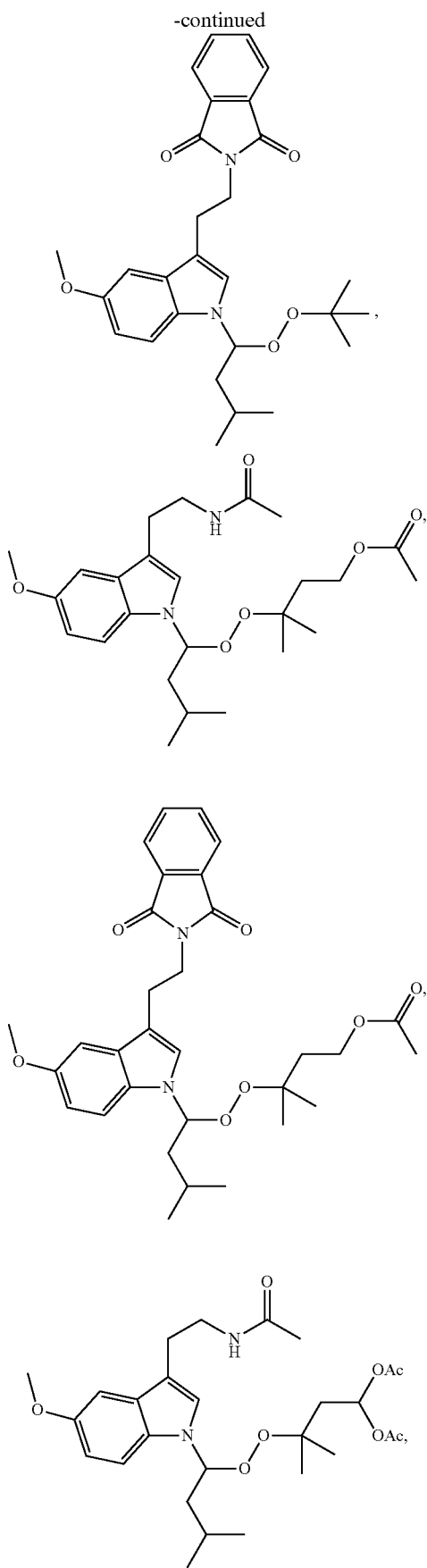

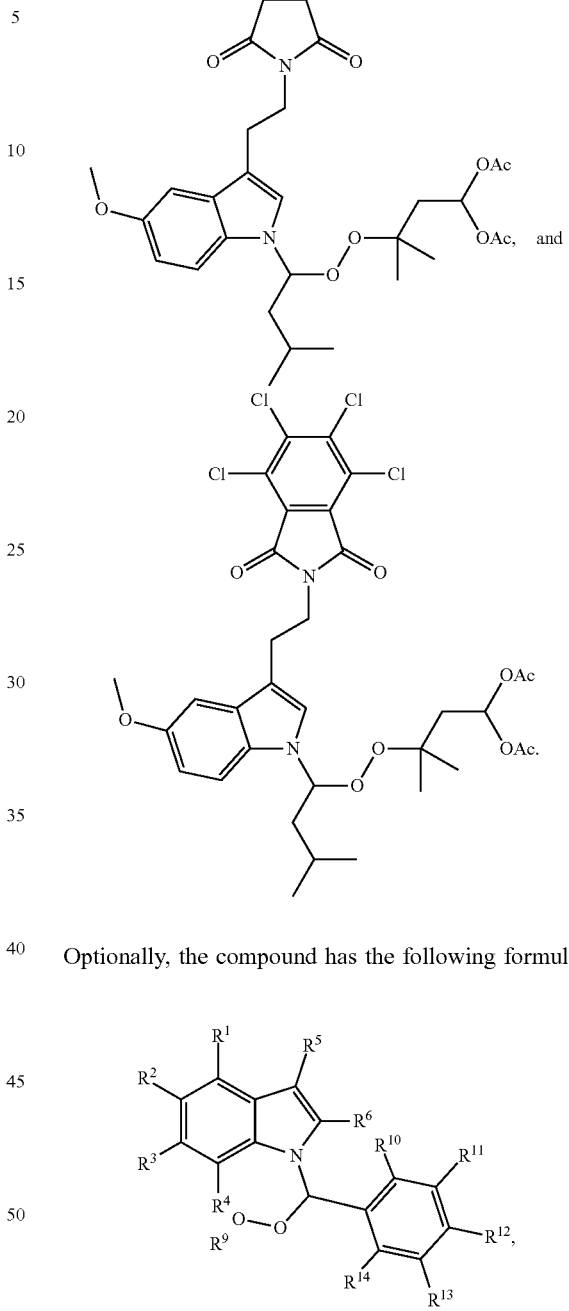

Optionally, the compound has the following formula:

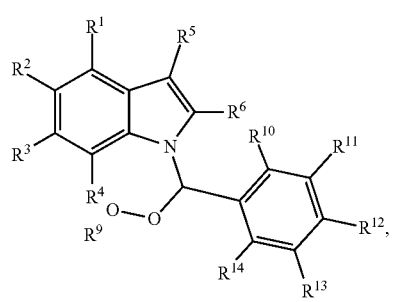

or a pharmaceutically acceptable salt or prodrug thereof, wherein $R^{10}$, $R^{11}$, $R^{12}$, $R^{13}$, and $R^{14}$ are each independently selected from hydrogen, halogen, cyano, trifluoromethyl, alkoxy, substituted or unsubstituted carbonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl. The compound can optionally be selected from the group consisting of

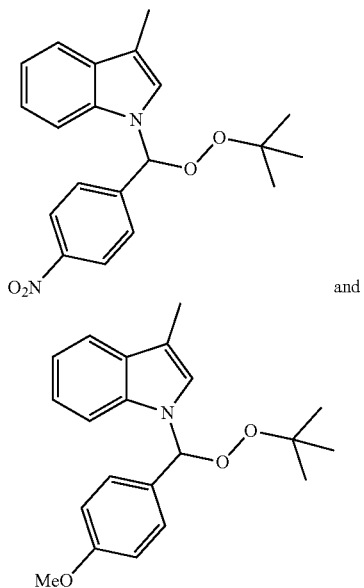

and

Also described herein are compositions comprising a compound as described herein and a pharmaceutically acceptable carrier.

Further described herein are methods of treating or preventing a parasitic infection in a subject. A method of treating or preventing a parasitic infection in a subject comprises administering to a subject an effective amount of a compound or a composition as described herein. Optionally, the parasitic infection is a *Plasmodium* infection (e.g., a *Plasmodium falciparum* infection). Optionally, the parasitic infection is malaria. The methods can further comprise administering to the subject an additional therapeutic agent (e.g., an anti-malarial agent).

Methods of treating or preventing a bacterial infection in a subject are also described herein. A method of treating or preventing a bacterial infection in a subject comprises administering to a subject an effective amount of a compound or a composition as described herein. The methods can further comprise administering to the subject an additional therapeutic agent (e.g., an anti-bacterial agent).

Also described herein are methods of treating or preventing cancer in a subject. A method of treating or preventing cancer in a subject comprises administering to a subject an effective amount of a compound or a composition as described herein. The methods can further comprise administering to the subject an additional therapeutic agent (e.g., an anti-cancer agent).

Methods of synthesizing N-(α-peroxy)indole compounds are also provided herein. A method of synthesizing an N-(α-peroxy)indole compound comprises reacting a carbonyl compound, an indole, and a peroxide in the presence of a catalyst. Optionally, the carbonyl compound is an aldehyde and/or the peroxide is a hydroperoxide. The catalyst can be an acid catalyst. Optionally, the reacting step is performed in the presence of a solvent.

The details of one or more embodiments are set forth in the description below. Other features, objects, and advantages will be apparent from the description and from the claims.

DETAILED DESCRIPTION

Provided herein are N-(α-peroxy)indole compounds and methods for their use. The N-(α-peroxy)indole compounds described herein are useful for treating or preventing parasitic infections, bacterial infections, and cancer in subjects. The methods include administering an N-(α-peroxy)indole compound as described herein to a subject. Also provided herein are methods for synthesizing N-(α-peroxy)indole compounds.

I. Compounds

A class of N-(α-peroxy)indole compounds described herein is represented by Formula I:

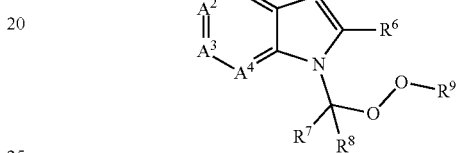

and pharmaceutically acceptable salts and prodrugs thereof.

In Formula I, $A^1$, $A^2$, $A^3$, and $A^4$ are each independently selected from CR and N. Each R is selected from the group consisting of hydrogen, halogen, cyano, trifluoromethyl, alkoxy, aryloxy, substituted or unsubstituted carbonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

Also in Formula I, $R^5$ and $R^6$ are each independently selected from hydrogen, halogen, cyano, trifluoromethyl, alkoxy, aryloxy, substituted or unsubstituted carbonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

Additionally in Formula I, $R^7$, $R^8$, and $R^9$ are each independently selected from hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

Optionally, in Formula I, adjacent R groups can be combined to form a cyclic compound, e.g., a substituted or unsubstituted aryl, substituted or unsubstituted cycloalkyl, substituted or unsubstituted cycloalkenyl, substituted or unsubstituted heteroaryl, substituted or unsubstituted heterocycloalkyl, or substituted or unsubstituted heterocycloalkenyl. In Formula I, $R^5$ and $R^6$ do not combine to form a cyclic compound.

Optionally, A1, A2, A3, and A4 are each independently selected from CR In these examples, Formula I can be represented by Structure I-A:

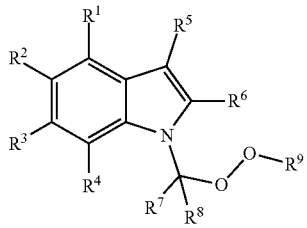

Structure I-A

In Structure I-A, $R^1$, $R^2$, $R^3$, $R^4$, $R^5$, and $R^6$ are each independently selected from hydrogen, halogen, cyano, trifluoromethyl, alkoxy, aryloxy, substituted or unsubstituted carbonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl. Optionally, $R^1$ is hydrogen. Optionally, $R^2$ is hydrogen or alkoxy. Optionally, $R^3$ is hydrogen. Optionally, $R^4$ is hydrogen. $R^5$ can optionally be substituted or unsubstituted alkyl. $R^6$ can optionally be hydrogen.

Also in Structure I-A, $R^7$, $R^8$, and $R^9$ are each independently selected from hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl. Optionally, $R^7$ is substituted or unsubstituted alkyl or substituted or unsubstituted aryl. $R^8$ can optionally be hydrogen. $R^9$ can optionally be substituted or unsubstituted alkyl.

Optionally, $R^7$ is isobutyl and $R^8$ is hydrogen. In these examples, Formula I can be represented by Structure 1-B:

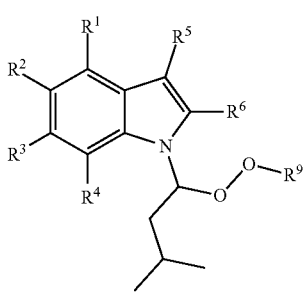

Structure 1-B

In Structure 1-B, $R^1$, $R^2$, $R^3$, $R^4$, $R^5$, $R^6$, and $R^9$ are as described above for Structure I-A.

Examples of Structure 1-B include the following compounds:

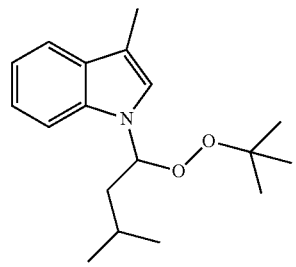

Compound 1

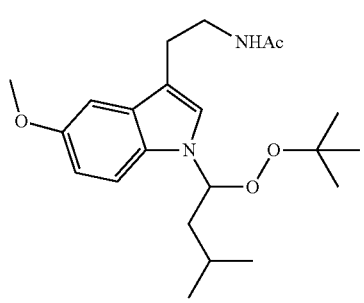

Compound 2

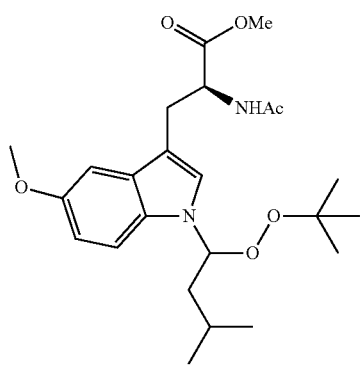

Compound 3

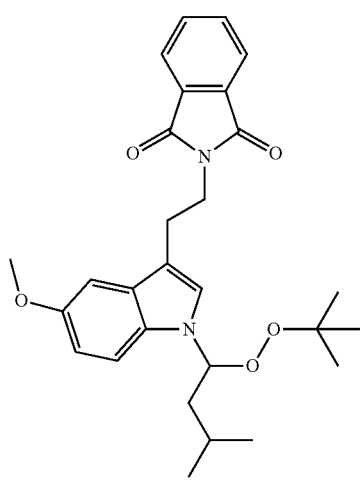

Compound 4

Compound 5
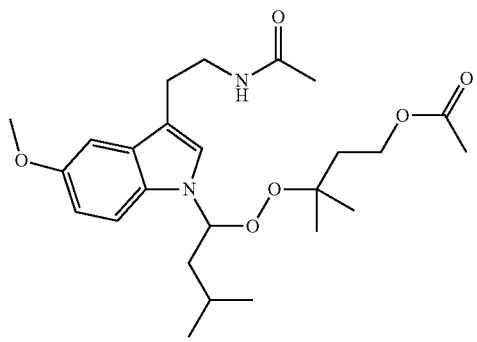

Compound 6
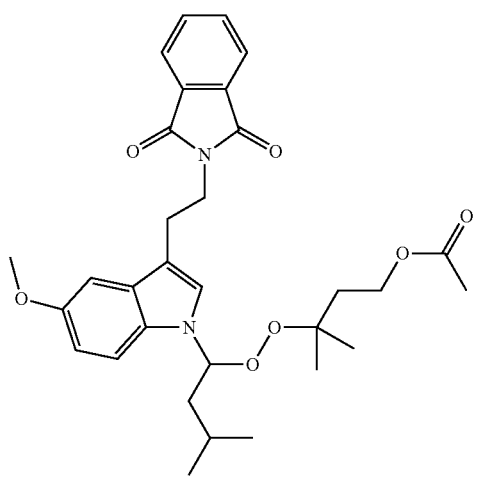

Compound 7
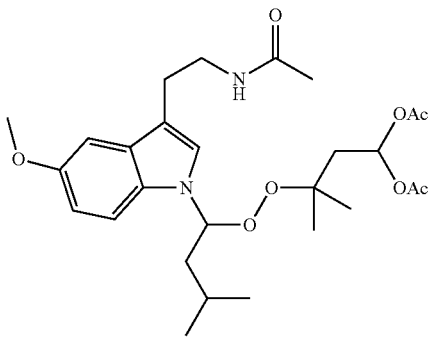

Compound 8
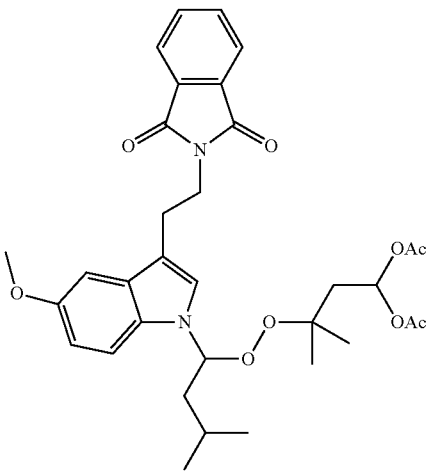

Compound 9
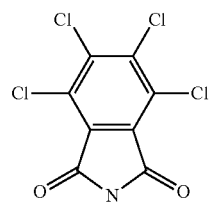
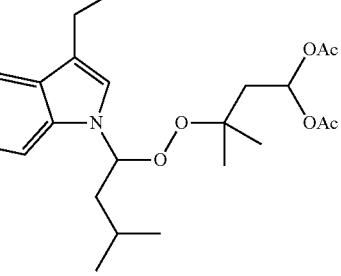

Optionally, $R^7$ is substituted or unsubstituted aryl and $R^8$ is hydrogen. In these examples, Formula I can be represented by Structure 1-C:

Structure 1-C
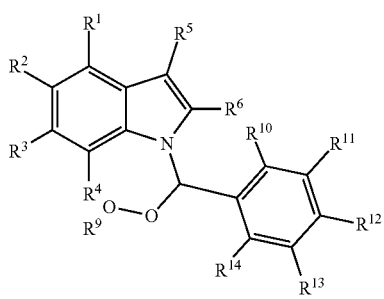

In Structure 1-C, $R^1$, $R^2$, $R^3$, $R^4$, $R^5$, $R^6$, and $R^9$ are as described above for Structure I-A.

Also in Structure 1-C, $R^{10}$, $R^{11}$, $R^{12}$, $R^{13}$, and $R^{14}$ are each independently selected from hydrogen, halogen, cyano, trifluoromethyl, alkoxy, substituted or unsubstituted carbonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

Examples of Structure 1-C include the following compounds:

Compound 10

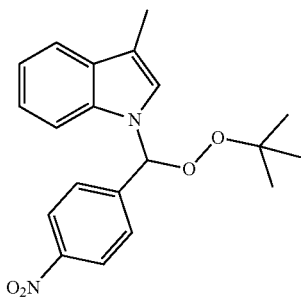

Compounds 11

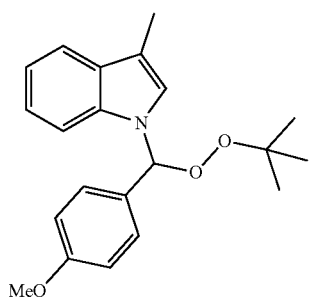

Optionally, at least one of $A^1$, $A^2$, $A^3$, and $A^4$ is N. In these examples, Formula I can be represented by Structure 1-D, Structure 1-E, Structure 1-F, or Structure 1-G:

Structure 1-D

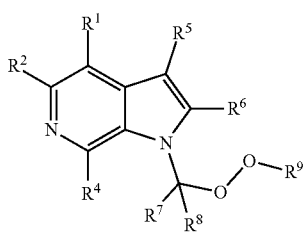

Structure 1-E

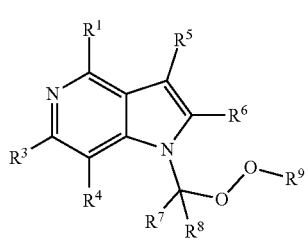

Structure 1-F

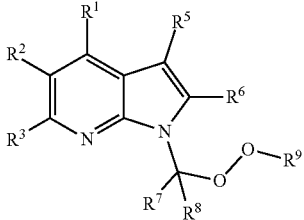

Structure 1-G

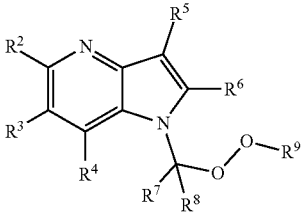

In Structure 1-D, Structure 1-E, Structure 1-F, and Structure 1-G, $R^1$, $R^2$, $R^3$, $R^4$, $R^5$, $R^6$, $R^7$, $R^8$, and $R^9$ are as described above for Structure I-A.

As used herein, the terms alkyl, alkenyl, and alkynyl include straight- and branched-chain monovalent substituents. Examples include methyl, ethyl, isobutyl, 3-butynyl, and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

Heteroalkyl, heteroalkenyl, and heteroalkynyl are defined similarly as alkyl, alkenyl, and alkynyl, but can contain O, S, or N heteroatoms or combinations thereof within the backbone. Ranges of these groups useful with the compounds and methods described herein include $C_1$-$C_{20}$ heteroalkyl, $C_2$-$C_{20}$ heteroalkenyl, and $C_2$-$C_{20}$ heteroalkynyl. Additional ranges of these groups useful with the compounds and methods described herein include $C_1$-$C_{12}$ heteroalkyl, $C_2$-$C_{12}$ heteroalkenyl, $C_2$-$C_{12}$ heteroalkynyl, $C_1$-$C_6$ heteroalkyl, $C_2$-$C_6$ heteroalkenyl, $C_2$-$C_6$ heteroalkynyl, $C_1$-$C_4$ heteroalkyl, $C_2$-$C_4$ heteroalkenyl, and $C_2$-$C_4$ heteroalkynyl.

The terms cycloalkyl, cycloalkenyl, and cycloalkynyl include cyclic alkyl groups having a single cyclic ring or multiple condensed rings. Examples include cyclohexyl, cyclopentylethyl, and adamantanyl. Ranges of these groups useful with the compounds and methods described herein include $C_3$-$C_{20}$ cycloalkyl, $C_3$-$C_{20}$ cycloalkenyl, and $C_3$-$C_{20}$ cycloalkynyl. Additional ranges of these groups useful with the compounds and methods described herein include $C_5$-$C_{12}$ cycloalkyl, $C_5$-$C_{12}$ cycloalkenyl, $C_5$-$C_{12}$ cycloalkynyl, $C_5$-$C_6$ cycloalkyl, $C_5$-$C_6$ cycloalkenyl, and $C_5$-$C_6$ cycloalkynyl.

The terms heterocycloalkyl, heterocycloalkenyl, and heterocycloalkynyl are defined similarly as cycloalkyl, cycloalkenyl, and cycloalkynyl, but can contain O, S, or N heteroatoms or combinations thereof within the cyclic backbone. Ranges of these groups useful with the compounds and methods described herein include $C_3$-$C_{20}$ heterocycloalkyl, $C_3$-$C_{20}$ heterocycloalkenyl, and $C_3$-$C_{20}$ heterocycloalkynyl. Additional ranges of these groups useful with the compounds and methods described herein include $C_5$-$C_{12}$ heterocycloalkyl, $C_5$-$C_{12}$ heterocycloalkenyl, $C_5$-$C_{12}$ heterocycloalkynyl, $C_5$-$C_6$ heterocycloalkyl, $C_5$-$C_6$ heterocycloalkenyl, and $C_5$-$C_6$ heterocycloalkynyl.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system. Examples of heteroaryl molecules include furan, pyrrole, thiophene, imadazole, oxazole, pyridine, and pyrazine. Aryl and heteroaryl molecules can also include additional fused rings, for example, benzofuran, indole, benzothiophene, naphthalene, anthracene, and quinoline. The aryl and heteroaryl molecules can be attached at any position on the ring, unless otherwise noted.

The term alkoxy as used herein is an alkyl group bound through a single, terminal ether linkage. The term aryloxy as used herein is an aryl group bound through a single, terminal ether linkage. Likewise, the terms alkenyloxy, alkynyloxy, heteroalkyloxy, heteroalkenyloxy, heteroalkynyloxy, heteroaryloxy, cycloalkyloxy, and heterocycloalkyloxy as used herein are an alkenyloxy, alkynyloxy, heteroalkyloxy, heteroalkenyloxy, heteroalkynyloxy, heteroaryloxy, cycloalkyloxy, and heterocycloalkyloxy group, respectively, bound through a single, terminal ether linkage.

The term hydroxy as used herein is represented by the formula —OH.

The terms amine or amino as used herein are represented by the formula-$NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The alkoxy, aryloxy, amino, alkyl, alkenyl, alkynyl, aryl, heteroalkyl, heteroalkenyl, heteroalkynyl, heteroaryl, cycloalkyl, or heterocycloalkyl molecules used herein can be substituted or unsubstituted. As used herein, the term substituted includes the addition of an alkoxy, aryloxy, amino, alkyl, alkenyl, alkynyl, aryl, heteroalkyl, heteroalkenyl, heteroalkynyl, heteroaryl, cycloalkyl, or heterocycloalkyl group to a position attached to the main chain of the alkoxy, aryloxy, amino, alkyl, alkenyl, alkynyl, aryl, heteroalkyl, heteroalkenyl, heteroalkynyl, heteroaryl, cycloalkyl, or heterocycloalkyl, e.g., the replacement of a hydrogen by one of these molecules. Examples of substitution groups include, but are not limited to, hydroxy, halogen (e.g., F, Br, Cl, or I), and carboxyl groups. Conversely, as used herein, the term unsubstituted indicates the alkoxy, aryloxy, amino, alkyl, alkenyl, alkynyl, aryl, heteroalkyl, heteroalkenyl, heteroalkynyl, heteroaryl, cycloalkyl, or heterocycloalkyl has a full complement of hydrogens, i.e., commensurate with its saturation level, with no substitutions, e.g., linear decane (—$(CH_2)_9$—$CH_3$).

II. Methods of Making the Compounds

The compounds described herein can be prepared in a variety of ways. The compounds can be synthesized using various synthetic methods. At least some of these methods include synthetic organic chemistry. The compounds described herein can be prepared from readily available starting materials. Optimum reaction conditions can vary with the particular reactants or solvent used, but such conditions can be determined by optimization procedures.

Variations on Formula I include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection, and the selection of appropriate protecting groups can be determined. The chemistry of protecting groups can be found, for example, in Greene and Wuts, Protective Groups in Organic Synthesis, 3rd. Ed., Wiley & Sons, 2002, which is incorporated herein by reference in its entirety.

Reactions to produce the compounds described herein can be carried out in solvents, which can be selected for organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored; for example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

The N-(α-peroxy)indole compounds described herein can be prepared according to Scheme 1 shown below.

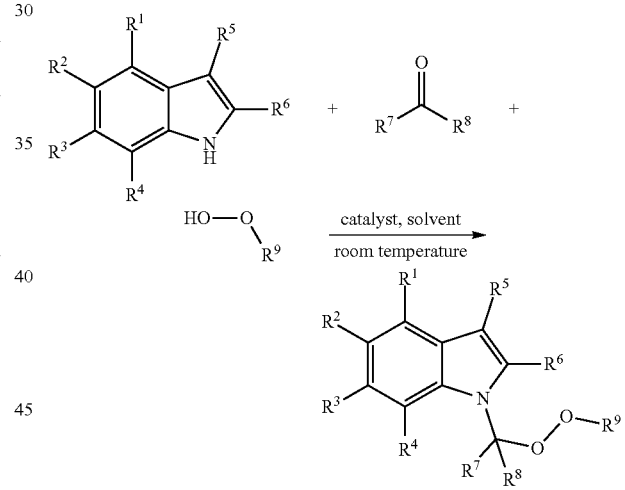

As shown in Scheme 1, an indole or indole derivative, a carbonyl compound, and a peroxide are reacted in the presence of a catalyst. The indole derivative can be, for example, an indoline compound (e.g., 3-methyl-indoline) or amino-protected histidine esters. Optionally, the carbonyl compound is an aldehyde, including aliphatic aldehydes or aromatic aldehydes, such as isoamyl aldehyde and benzaldehyde. Optionally, the carbonyl compound is a ketone. The peroxide can be a hydroperoxide or a protected peroxide, such as a trimethylsilyl (TMS)-protected peroxide. The ratio of indole to carbonyl to peroxide can optionally be 1 part indole to 2 parts carbonyl to 3 parts peroxide.

The catalyst can be an acid catalyst, such as p-toluenesulfonic acid (PTSA). The reaction can be performed in the presence of a solvent. Suitable solvents include, for example, halogenated solvents, such as dichloromethane, dichloroethane, and chloroform, and other aprotic solvents. The reaction can be performed for a period of time. Optionally, the reaction can be performed for a period up to 24 hours (e.g., 1 minute, 5 minutes, 10 minutes, 15 minutes, 20 minutes, 25 minutes, 30 minutes, 35 minutes, 40 minutes, 45 minutes, 1 hour, 2 hours, 4 hours, 6 hours, 8 hours, 10 hours, 12 hours, 14 hours, 16 hours, 18 hours, 20 hours, 22 hours, or 24 hours, inclusive).

Exemplary methods for synthesizing the compounds as described herein are provided in Example 1 below.

III. Pharmaceutical Formulations

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other materials for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22d Edition, Loyd et al. eds., Pharmaceutical Press and Philadelphia College of Pharmacy at University of the Sciences (2012). Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.).

Compositions containing the compound described herein or derivatives thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hardfilled gelatin capsules using such excipients as lactose or milk sugar as well as high molecular weight polyethylene glycols, and the like.

Solid dosage forms such as tablets, dragees, capsules, pills, and granules can be prepared with coatings and shells, such as enteric coatings. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents, such as water or other solvents, solubilizing agents, and emulsifiers, as for example, ethyl alcohol, isopropyl alcohol, ethyl carbonate, ethyl acetate, benzyl alcohol, benzyl benzoate, propylene glycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethylene glycols, and fatty acid esters of sorbitan, or mixtures of these substances, and the like.

Besides such inert diluents, the composition can also include additional agents, such as wetting, emulsifying, suspending, sweetening, flavoring, or perfuming agents. Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers, such as cocoa butter, polyethylene glycol or a suppository wax, which are solid at ordinary temperatures but liquid at body temperature and, therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., J. Pharm. Sci. (1977) 66, 1, which is incorporated herein by reference in its entirety, at least, for compositions taught therein.)

Administration of the compounds and compositions described herein or pharmaceutically acceptable salts thereof can be carried out using therapeutically effective amounts of the compounds and compositions described herein or pharmaceutically acceptable salts thereof as described herein for periods of time effective to treat a disorder. The effective amount of the compounds and compositions described herein or pharmaceutically acceptable salts thereof as described herein may be determined and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.01 to about 50 mg/kg of body weight of active compound per day, about 0.05 to about 25 mg/kg of body weight of active compound per day, about 0.1 to about 25 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, about 5 mg/kg of body weight of active compound per day, about 2.5 mg/kg of body weight of active compound per day, about 1.0 mg/kg of body weight of active compound per day, or about 0.5 mg/kg of body weight of active compound per day, or any range derivable therein. Optionally, the dosage amounts are from about 0.01 mg/kg to about 10 mg/kg of body weight of active compound per day. Optionally, the dosage amount is from about 0.01 mg/kg to about 5 mg/kg. Optionally, the dosage amount is from about 0.01 mg/kg to about 2.5 mg/kg.

The specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems. Further, the route of administration would assist in determination of doses that result in a plasma concentration for a desired level of response in the cells, tissues and/or organs of a subject.

IV. Methods of Use

Provided herein are methods to treat, prevent, or ameliorate parasitic infections, bacterial infections, and/or cancer in a subject. The methods include administering to a subject an effective amount of one or more of the compounds or compositions described herein or a pharmaceutically acceptable salt or prodrug thereof. The method can include selecting a subject with a parasitic infection, a bacterial infection, or cancer. The expression "effective amount," when used to describe an amount of compound in a method, refers to the amount of a compound that achieves the desired pharmacological effect or other effect, for example, an amount that results in infection reduction or tumor growth rate reduction. The compounds and compositions described herein or pharmaceutically acceptable salts thereof are useful for treating parasitic infections, bacterial infections, and/or cancer in humans, including, without limitation, pediatric and geriatric populations, and in animals, e.g., veterinary applications.

Optionally, the parasitic infection is a *Plasmodium* infection, such as a *Plasmodium falciparum* infection. Optionally, the parasitic infection is malaria. Optionally, the parasitic infection is a *Toxoplarma gondii* infection, a *Leishmania* infection, or a *Babesia* infection.

Optionally, the bacterial infection is a Gram-negative bacterial infection, such as an *Acinetobacter* infection (e.g., an *Acinetobacter baumannii* infection), a *Pseudomonas* infection (e.g., a *Pseudomonas aeruginosa* infection), a *Klebsiella* infection, an *Escherichia* infection, a *Salmonella* infection, a *Yersinia* infection, a *Shigella* infection, a *Proteus* infection, an *Enterobacter* infection, a *Serratia* infection, or a *Citrobacter* infection. In some examples, the microbial infection is a Gram-positive bacterial infection, such as a *Bacillus* infection, a *Listeria* infection, a *Staphylococcus* infection, a *Streptococcus* infection, an *Enterococcus* infection, or a *Clostridium* infection.

Optionally, the cancer is bladder cancer, brain cancer, breast cancer, colorectal cancer (e.g., colon cancer, rectal cancer), cervical cancer, chondrosarcoma, endometrial cancer, gastrointestinal cancer, gastric cancer, genitourinary cancer, head and neck cancer, hepatocellular carcinoma, liver cancer, lung cancer, ovarian cancer, pancreatic cancer, prostate cancer, renal cancer, skin cancer, or testicular cancer.

The method of treating or preventing parasitic infections, bacterial infections, and/or cancer in a subject can further comprise administering to the subject one or more additional therapeutic agents. The one or more additional agents and the compounds described herein or pharmaceutically acceptable salts or prodrugs thereof can be administered in any order, including concomitant, simultaneous, or sequential administration. Sequential administration can be temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

Therapeutic agents include, but are not limited to, antimalarial agents. An antimalarial agent is a compound or composition effective in inhibiting or arresting the activity of a *Plasmodium* parasite. Suitable antimalarial agents include, for example, chloroquine, quinine, mefloquine, amodiaquin, primaquine, pyrimethamine, sulfonamides, sulfones, dihydrofolate reductase inhibitors, and tetrandine.

Antibacterial agents can also be used as the therapeutic agents. Suitable antibacterial agents can include any agent effective for treating a bacterial infection and include, for example, tetracyclines (e.g., minocycline), quinolones (e.g., ciprofloxacin, levofloxacin, and nalidixic acid), aminoglycosides (e.g., amikacin, gentamycin, kanamycin, and tobramycin), carbapenems (e.g., meropenem), cephalosporins (e.g., ceftriaxone), macrolides (e.g., erythromycin), polypeptides (e.g., colistin and polymxin B), sulfonamides (e.g., sulfamethoxazole), glycylcyclines (e.g., tigecycline), beta lactams (e.g., penams), lipopeptides (e.g., daptomycin), oxazolidinones (e.g., linezolid), and trimethoprim.

Therapeutic agents further include, but are not limited to, chemotherapeutic agents. A chemotherapeutic agent is a compound or composition effective in inhibiting or arresting the growth of an abnormally growing cell. Thus, such an agent may be used therapeutically to treat cancer as well as other diseases marked by abnormal cell growth. Illustrative examples of chemotherapeutic compounds include, but are not limited to, bexarotene, gefitinib, erlotinib, gemcitabine, paclitaxel, docetaxel, topotecan, irinotecan, temozolomide, carmustine, vinorelbine, capecitabine, leucovorin, oxaliplatin, bevacizumab, cetuximab, panitumumab, bortezomib, oblimersen, hexamethylmelamine, ifosfamide, CPT-11, deflunomide, cycloheximide, dicarbazine, asparaginase, mitotant, vinblastine sulfate, carboplatin, colchicine, etoposide, melphalan, 6-mercaptopurine, teniposide, vinblastine, antibiotic derivatives (e.g. anthracyclines such as doxorubicin, liposomal doxorubicin, and diethylstilbestrol doxorubicin, bleomycin, daunorubicin, and dactinomycin); antiestrogens (e.g., tamoxifen); antimetabolites (e.g., fluorouracil (FU), 5-FU, methotrexate, floxuridine, interferon alpha-2B, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cisplatin, vincristine and vincristine sulfate); hormones (e.g., medroxyprogesterone, estramustine phosphate sodium, ethinyl estradiol, estradiol, megestrol acetate, methyl testosterone, diethylstilbestrol diphosphate, chlorotrianisene, and testolactone); nitrogen mustard derivatives (e.g., mephalen, chlorambucil, mechlorethamine (nitrogen mustard) and thiotepa); and steroids (e.g., bethamethasone sodium phosphate).

The methods and compounds as described herein are useful for both prophylactic and therapeutic treatment. For prophylactic use, a therapeutically effective amount of the compounds and compositions or pharmaceutically acceptable salts thereof as described herein are administered to a subject prior to onset (e.g., before obvious signs of a parasitic infection, a bacterial infection, or cancer), during early onset (e.g., upon initial signs and symptoms of a parasitic infection, a bacterial infection, or cancer), or after the development of a parasitic infection, a bacterial infection, or cancer. Prophylactic administration can occur for several days to years prior to the manifestation of symptoms of a parasitic infection, a bacterial infection, or cancer. Therapeutic treatment involves administering to a subject a therapeutically effective amount of the compounds and compositions or pharmaceutically acceptable salts thereof as described herein after a parasitic infection, a bacterial infection, or cancer is diagnosed.

V. Kits

Also provided herein are kits for treating or preventing parasitic infections, bacterial infections, and/or cancer in a subject. A kit can include any of the compounds or compositions described herein. For example, a kit can include a compound of Formula I. A kit can further include one or more additional agents, such as one or more anti-malarial, anti-bacterial, or anti-cancer agents. A kit can include an oral formulation of any of the compounds or compositions described herein. A kit can include an intravenous formulation of any of the compounds or compositions described herein. A kit can additionally include directions for use of the kit (e.g., instructions for treating a subject), a container, a means for administering the compounds or compositions (e.g., a syringe), and/or a carrier. A kit can include multiple metered dosages for a course of treatment with the compound of Formula I, with or without any additional therapeutic agents.

As used herein the terms treatment, treat, or treating refer to a method of reducing one or more symptoms of an infection, disease, or condition. Thus in the disclosed method, treatment can refer to a 10%, 20%, 30%, 40%, 50%, 60%, 70%, 80%, 90%, or 100% reduction in the severity of one or more symptoms of the infection, disease, or condition. For example, a method for treating an infection, disease, or condition is considered to be a treatment if there is a 10% reduction in one or more symptoms or signs of the infection, disease, or condition in a subject as compared to a control. As used herein, control refers to the untreated infection, disease, or condition. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the infection, disease, condition, or symptoms of the infection, disease or condition.

As used herein, the terms prevent, preventing, and prevention of an infection, disease, or disorder refer to an action, for example, administration of a composition or therapeutic agent, that occurs before or at about the same time a subject begins to show one or more symptoms of the infection, disease, or disorder, which inhibits or delays onset or severity of one or more symptoms of the infection, disease, or disorder. For example, the method is considered to be a prevention if there is a reduction or delay in onset, incidence, severity or recurrence of infection or cancer, or one or more symptoms of infection (e.g., fever, chills, vomiting, or convulsions) or cancer (e.g., tumor growth) in a subject susceptible to infection or cancer compared to control subjects susceptible to infection or cancer that did not receive a compound as described herein. The reduction or delay in onset, incidence, severity, or recurrence of infection or cancer can be a 10%, 20%, 30%, 40%, 50%, 60%, 70%, 80%, 90%, 100%, or any percent reduction in between 10% and 100% as compared to native or control levels.

As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

Throughout this application, various publications are referenced. The disclosures of these publications in their entireties are hereby incorporated by reference into this application. The examples below are intended to further illustrate certain aspects of the methods and compositions described herein, and are not intended to limit the scope of the claims.

EXAMPLES

Example 1: Synthesis of Compounds

General Experimental Procedures:

All reagents and solvents were purchased at the highest commercial quality and used as received unless otherwise specified. Reactions were carried out in an open flask without inert protection, unless otherwise noted. Analytical thin-layer chromatography (TLC) was performed on 0.25 mm coated silica gel plates (60E-254) purchased from Qingdao Haiyang Chemical Co., Ltd and visualized by exposure to UV light (254 nm) or stained with potassium permanganate ($KMnO_4$) and ethanolic phosphomolybdic acid (PMA). $^1H$ NMR spectra were acquired on a Bruker AVANCE (at 400 MHz, 500 MHz, or 600 MHz) and chemical shifts are reported relative to the residual solvent peak. The following abbreviations were used to describe the data of $^1H$ NMR spectra: chemical shift (δ ppm), s=singlet, d=doublet, t=triplet, q=quartet, m=multiplet, br=broad; coupling constant(s) in Hz. $^{13}C$ NMR spectra were acquired on a Bruker AVANCE (at 100 MHz, 125 MHz, or 150 MHz) and chemical shifts (δ ppm) are reported relative to the residual solvent peak. High-resolution mass spectrometry (HRMS) data were acquired using Bruker MALDI TOF or BrukerDaltonicsMicroTOF-Q-11 Mass Spectrometer.

Preparation of Anhydrous Tert-Butyl Hydroperoxide (tBuOOH):

Commercial 70% aqueous tBuOOH (50 mL) was added into 200 mL anhydrous diethyl ether, and was slowly shaken. The mixture was separated via a separating funnel. The organic phase was washed twice with 30 mL of a saturated NaCl solution and dried with anhydrous $MgSO_4$. Removal of diethyl ether by vacuum rotation evaporation gave anhydrous tBuOOH, which could be stored at low temperature (<−20° C.).

Standard Procedure for the Synthesis of N-(α-peroxy)-indole:

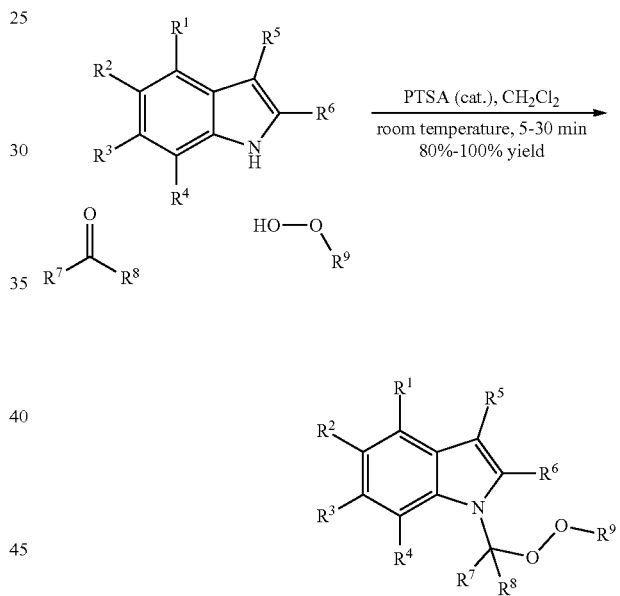

To a stirred solution of indole (1.0 mmol), carbonyl (2.0 mmol), and hydroperoxide (3 mmol) in $CH_2Cl_2$ (5 mL) in an open 25 mL glass flask at room temperature was added p-toluenesulfonic acid monohydrate (PTSA-$H_2O$, 10 mol %) as solid in one portion. The reaction mixture changed color immediately and the reaction generally finished within a few seconds. However, to be more practically convenient, and for aromatic aldehydes, the reaction was allowed to continue, followed by stirring for 5-30 minutes. Then, the reaction mixture was neutralized with $NaHCO_3$ (aq.), extracted with $CH_2Cl_2$, and washed by saturated brine. The organic phase was dried with $MgSO_4$, followed by vacuum rotation evaporation, to remove the solvent. Purification by flash column chromatography (EtOAc/hexane) on silica gel gave the titled product.

Synthetic Procedures and Characterization for Compounds 1-12:

Representative Large Scale Synthesis of 1-(1-(tert-butylperoxy)-3-methylbutyl)-3-methyl-indole.

Compound 1

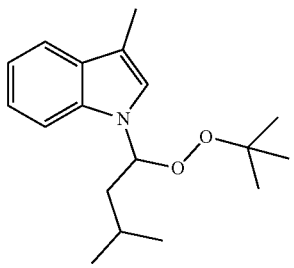

To a stirred solution of 3-methyl-indole (2.6 g, 20 mmol), 3-methylbutanal (3.5 g, 40 mmol), and tBuOOH (5.4 g, 60 mmol) in CH$_2$Cl$_2$ (100 mL) in an 250 mL glass flask at room temperature was added PTSA (35 mg, 0.2 mmol) in two successive portions. After stirring for 30 minutes at room temperature under air, the reaction mixture was neutralized with NaHCO$_3$ (aq.), and extracted with CH$_2$Cl$_2$ (3×100 mL). The organic phase was collected and dried over anhydrous MgSO$_4$, followed by vacuum rotation evaporation to remove the solvent. The crude product was then purified by flash column chromatography (EtOAc/hexane 1:20 v/v) to give the 1-(1-(tert-butylperoxy)-3-methylbutyl)-3-methyl-indole, 5.73 g in 99% yield, as a colorless oil. $^1$H NMR (500 MHz, CDCl$_3$) δ 7.55-7.54 (d, 1H), 7.48-7.46 (d, 1H), 7.22-7.20 (t, 1H), 7.13-7.10 (m, 1H), 7.03 (s, 1H), 2.33 (s, 3H), 2.02-1.89 (m, 2H), 1.62-1.60 (m, 1H), 1.02 (s, 9H), 0.95-0.93 (dd, 6H); $^{13}$C NMR (125 MHz, CDCl$_3$) δ 137.21, 129.14, 121.93, 121.56, 119.04, 118.80, 111.78, 110.14, 86.56, 80.50, 40.85, 26.16, 24.88, 22.84, 22.43, 9.71 ppm. HRMS (m/z): calculated for C$_{18}$H$_{28}$NO$_2$ [M+H]$^+$ 290.2115; found 290.2118.

Compound 2

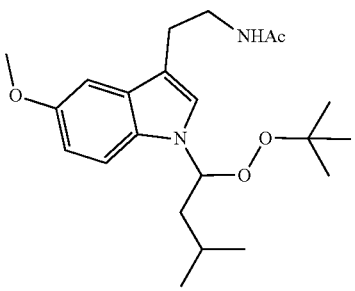

Compound 2 was prepared using the standard procedure described above. The product was obtained as a colorless oil, 330 mg, 85% yield. Hexane:EtOAc 2:1. $^1$H NMR (500 MHz, CDCl$_3$) δ 7.40-7.38 (d, 1H), 7.07 (s, 1H), 7.01-7.00 (d, 1H), 6.89-6.87 (q, 1H), 5.94-5.91 (t, 1H), 5.58 (b, 1H, NH), 3.86 (s, 3H), 3.67-3.56 (q, 2H), 2.95-2.91 (m, 2H), 1.98-1.88 (m, 5H), 1.60-1.55 (m, 1H), 1.00 (s, 9H), 0.94-0.93 (dd, 6H); $^{13}$C NMR (125 MHz, CDCl$_3$) δ 170.04, 154.08, 132.47, 128.40, 123.04, 112.50, 112.06, 111.32, 100.60, 86.83, 80.52, 55.84, 40.68, 39.62, 26.11, 25.25, 24.92, 23.25, 22.75, 22.40 ppm. HRMS (m/z): calculated for C$_{22}$H$_{35}$N$_2$O$_4$ [M+H]$^+$ 391.2591; found 391.2592.

Compound 3

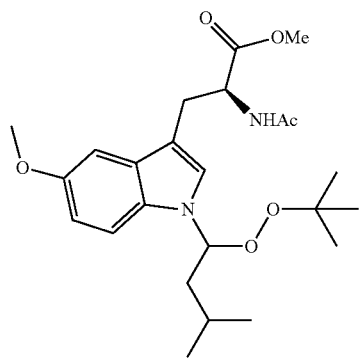

Compound 3 was prepared using the standard procedure described above. The product was obtained as a colorless oil, 402 mg, 96% yield, dr=1:1, Hexane:EtOAc 5:1. $^1$H NMR (400 MHz, CDCl$_3$) δ 7.51-7.48 (m, 2H), 7.23-7.20 (m, 1H), 7.19-7.11 (m, 1H), 7.08-7.07 (d, 1H), 6.02-5.97 (m, 1H), 5.25-5.24 (b, 1H), 4.72-4.69 (b, 1H), 3.67 (s, 6H), 3.31-3.29 (t, 2H), 2.00-1.91, (m, 2H), 1.59-1.53 (m, 2H), 0.99-0.98 (d, 9H), 0.95-0.92 (m, 6H); $^{13}$C NMR (100 MHz, CDCl$_3$) δ 172.45, 172.34, 156.37, 136.98, 136.92, 128.19, 123.28, 123.14, 121.99, 119.67, 118.57, 110.49, 110.39, 109.95, 86.54, 86.39, 80.54, 77.32, 77.00, 76.68, 54.40, 54.33, 52.23, 52.20, 40.58, 27.99, 27.94, 26.02, 24.82, 24.77, 22.76, 22.74, 22.34, 22.32 ppm. HRMS (m/z): calculated for C$_{23}$H$_{35}$N$_2$O$_5$ [M+H]$^+$ 419.2540; found 419.2539.

Compound 4

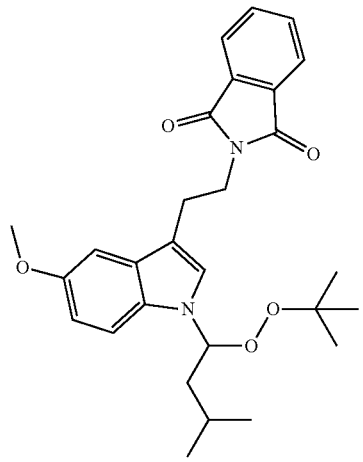

Compound 4 was prepared using the standard procedure described above. The product was obtained as a colorless solid, 473 mg, 99% yield, Hexane:EtOAc 8:1. $^1$H NMR (500 MHz, CDCl$_3$) δ 7.85-7.84 (t, 2H), 7.72-7.70 (q, 2H), 7.38-7.36 (d, 1H), 7.17-7.12 (d, 2H), 6.87-6.85 (q, 1H), 5.91-5.88 (t, 1H), 4.01-3.98 (t, 2H), 3.13-3.10 (q, 2H), 1.97-1.85 (m, 2H), 1.57-1.52 (m, 1H), 0.97 (s, 9H), 0.91-0.90 (dd, 6H); $^{13}$C NMR (125 MHz, CDCl$_3$) δ 168.20, 154.03, 133.75, 132.26, 132.20, 128.47, 123.06, 123.02, 112.07, 111.87, 111.18, 100.48, 86.77, 80.41, 77.25, 77.00, 76.75, 55.70, 40.56, 38.22, 26.04, 24.81, 24.43, 22.74, 22.30 ppm. HRMS (m/z): calculated for C$_{28}$H$_{35}$N$_2$O$_5$ [M+H]$^+$ 479.2540; found 479.2543.

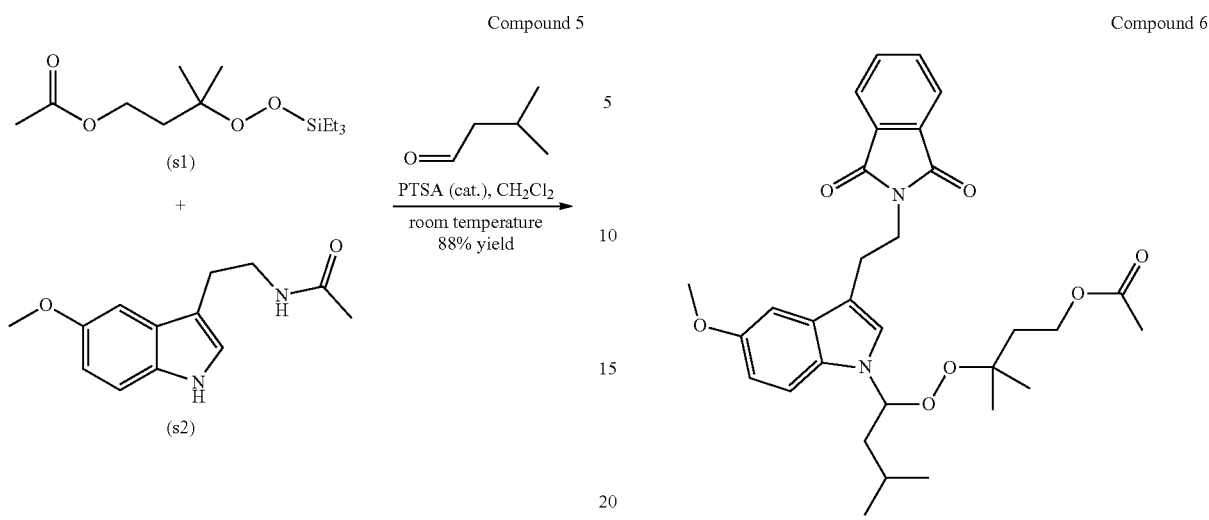

Compound 5

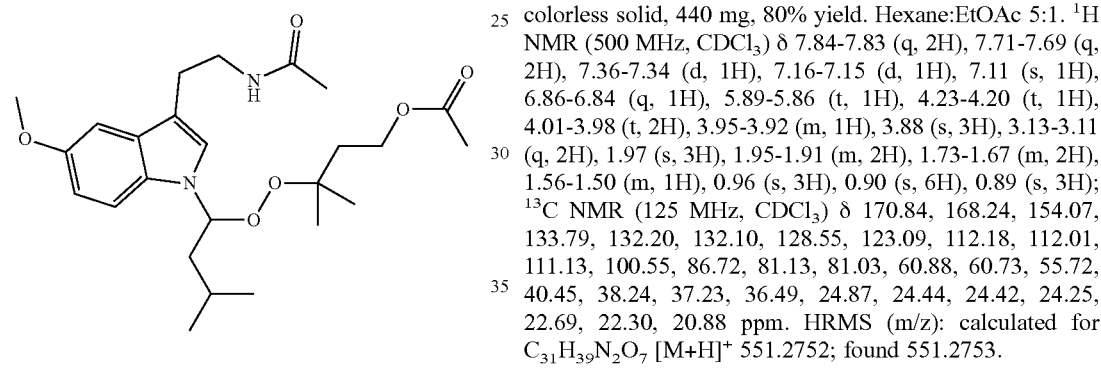

To a mixture of peroxide s1 (1.4 g, 5 mmol), aldehyde (860 mg, 10 mmol) and indole derivative s2 (232 mg, 1 mol) in 10 mL $CH_2Cl_2$ was added PTSA (18 mg). The mixture was stirred at room temperature for 10 minutes. Then the reaction mixture was neutralized with $NaHCO_3$ (aq.), and extracted with $CH_2Cl_2$ (3×100 mL). The organic phase was collected and dried over anhydrous $Na_2SO_4$, followed by vacuum rotation evaporation to remove the solvent. The crude product was then purified by flash column chromatography (ethyl acetate/hexane 1:2 v/v) to give Compound 5 (407 mg, 88% yield) as a colorless oil. $^1$H NMR (500 MHz, $CDCl_3$) δ 7.39-7.37 (d, 1H), 7.03 (s, 1H), 6.99-6.98 (d, 1H), 6.88-6.86 (q, 1H), 5.09 (b, 1H, NH), 5.88-5.85 (t, 1H), 3.86 (s, 3H), 3.81-3.75 (m, 1H), 3.66-3.64 (m, 1H), 3.60-3.56 (m, 2H), 2.95-2.92 (m, 2H), 1.98-1.87 (m, 8H), 1.76-1.67 (m, 2H), 1.58-1.53 (m, 1H), 1.06-0.96 (q, 12H); $^{13}$C NMR (125 MHz, $CDCl_3$) δ 170.97, 170.22, 154.13, 132.03, 128.79, 123.48, 112.74, 112.09, 111.38, 100.79, 87.06, 80.96, 60.67, 55.83, 40.52, 39.79, 37.00, 25.15, 25.01, 24.82, 24.47, 23.18, 22.67, 22.38, 20.82 ppm. HRMS (m/z): calculated for $C_{25}H_{39}N_2O_6$ $[M+H]^+$ 463.2803; found 463.2805.

Compound 6

Compound 6 was obtained using a similar procedure as used for Compound 5. The product was obtained as a colorless solid, 440 mg, 80% yield. Hexane:EtOAc 5:1. $^1$H NMR (500 MHz, $CDCl_3$) δ 7.84-7.83 (q, 2H), 7.71-7.69 (q, 2H), 7.36-7.34 (d, 1H), 7.16-7.15 (d, 1H), 7.11 (s, 1H), 6.86-6.84 (q, 1H), 5.89-5.86 (t, 1H), 4.23-4.20 (t, 1H), 4.01-3.98 (t, 2H), 3.95-3.92 (m, 1H), 3.88 (s, 3H), 3.13-3.11 (q, 2H), 1.97 (s, 3H), 1.95-1.91 (m, 2H), 1.73-1.67 (m, 2H), 1.56-1.50 (m, 1H), 0.96 (s, 3H), 0.90 (s, 6H), 0.89 (s, 3H); $^{13}$C NMR (125 MHz, $CDCl_3$) δ 170.84, 168.24, 154.07, 133.79, 132.20, 132.10, 128.55, 123.09, 112.18, 112.01, 111.13, 100.55, 86.72, 81.13, 81.03, 60.88, 60.73, 55.72, 40.45, 38.24, 37.23, 36.49, 24.87, 24.44, 24.42, 24.25, 22.69, 22.30, 20.88 ppm. HRMS (m/z): calculated for $C_{31}H_{39}N_2O_7$ $[M+H]^+$ 551.2752; found 551.2753.

Compound 7

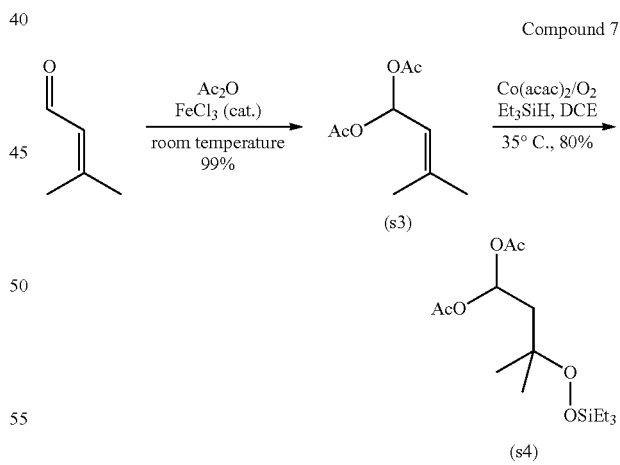

Synthesis of peroxide (s3): Prenal (1.2 g, 14.7 mmol) was added to freshly distilled $Ac_2O$ (2.7 g, 26 mmol) and the mixture was stirred at room temperature for 15 minutes. Then, anhydrous $FeCl_3$ (70 mg, 0.43 mmol, 3 mol %) was added carefully. After stirring at room temperature for another 20 minutes, the mixture was poured into a mixture of 25 mL n-hexane and 10 mL water, and was then extracted with hexane and washed with brine three times. The organic phase was collected and dried over anhydrous $Na_2SO_4$, followed by vacuum rotation evaporation to remove the solvent. The obtained colorless product was found to have >95% purity by NMR, and was used in the next step without further purification. $^1$H NMR (400 MHz, CDCl$_3$) δ 7.40-7.38 (d, J=8.4 Hz, 1H), 5.31-5.28 (m, 1H), 2.07 (s, 6H), 1.83-1.82 (d, J=1.2 Hz, 3H), 1.77-1.76 (d, J=1.2 Hz, 3H); $^{13}$C NMR (100 MHz, CDCl$_3$) δ 168.74, 141.91, 118.74, 87.52, 25.72, 20.85, 18.63 ppm.

Synthesis of peroxide (s4): To a mixture of compound s3 (225 mg, 1.2 mmol) dissolved in 6 mL freshly distilled and dried 1,2-dichloroethane (DCE) was added Co(acac)$_2$. The reaction vial was then degassed with oxygen and protected with an oxygen balloon. Et$_3$SiH was then added and the mixture was kept in an oil bath at 35° C. for 4 hours. The mixture was filtered and the filtrate was extracted with EtOAc (20 mL×3), washed with brine, dried with anhydrous Na$_2$SO$_4$, and evaporated with vacuum rotation evaporation. The crude product was purified by flash column chromatography (hexane/EtOAc 20:1 v/v) to give peroxide (s4) in an 80% yield as a colorless oil. $^1$H NMR (500 MHz, CDCl$_3$) δ 6.96-6.94 (t, 1H), 2.12-2.10 (d, 2H), 2.05 (s, 6H), 1.24 (s, 6H), 0.99-0.96 (t, 9H), 0.69-0.64 (q, 6H); $^{13}$C NMR (125 MHz, CDCl$_3$) δ 168.56, 88.70, 80.26, 42.01, 24.76, 20.84, 6.67, 3.78 ppm.

was added in one portion. The reaction was quenched after 3 minutes at room temperature, washed with brine, and extracted with EtOAc. The collected organic phase was dried with anhydrous Na$_2$SO$_4$ and evaporated with vacuum rotation evaporation. The crude product was purified by flash column chromatography (hexane/EtOAc 1:2 v/v) to give 55 mg of Compound 7 in 48% yield as colorless oil. Compound 7 was found to not be stable in CDC13, as it decomposed within the NMR tube in one day at room temperature. $^1$H NMR (500 MHz, CDCl$_3$) δ 7.37-7.36 (d, 1H), 7.06 (s, 1H), 6.99-6.98 (d, 1H), 6.87-6.85 (q, 1H), 6.72-6.70 (t, 1H), 5.97 (b, 1H, NH), 5.91-5.89 (t, 1H), 3.86 (s, 3H), 3.60-3.57 (q, 2H), 2.94-2.91 (m, 2H), 1.95-1.86 (m, 13H), 1.59-1.53 (m, 1H), 1.11 (s, 3H), 1.01 (s, 3H), 0.94-0.92 (q, 6H); $^{13}$C NMR (125 MHz, CDCl$_3$) δ 168.57, 168.53, 154.15, 131.97, 128.87, 123.56, 112.79, 112.06, 111.37, 100.76, 89.34, 88.24, 87.22, 80.37, 80.20, 55.99, 55.87, 52.60, 42.11, 41.00, 40.66, 39.87, 25.19, 24.95, 24.90, 24.45, 23.51, 22.67, 22.56, 22.44, 20.86, 20.72, 20.67 ppm. HRMS (m/z): calculated for C$_{27}$H$_{41}$N$_2$O$_8$ [M+H]$^+$ 521.2857; found 521.2855.

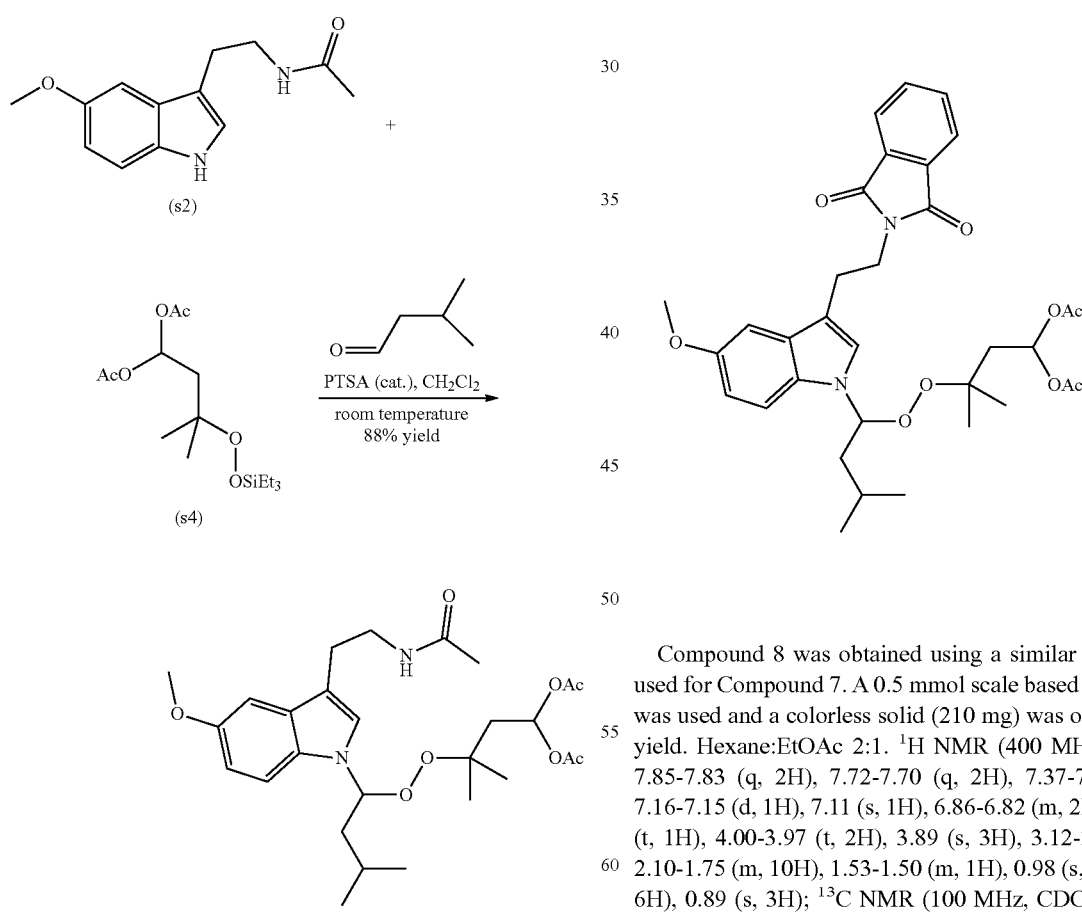

A mixture of isovaleraldehyde (190 mg, 2.2 mmol), indole (s2) (52 mg, 0.22 mmol), and peroxide (s4) (225 mg, 0.66 mmol) in 3 mL dichloromethane was stirred at room temperature for 5 minutes. Then, PTSA (37 mg, 0.22 mmol)

Compound 8 was obtained using a similar procedure as used for Compound 7. A 0.5 mmol scale based on the indole was used and a colorless solid (210 mg) was obtained, 69% yield. Hexane:EtOAc 2:1. $^1$H NMR (400 MHz, CDCl$_3$) δ 7.85-7.83 (q, 2H), 7.72-7.70 (q, 2H), 7.37-7.35 (d, 1H), 7.16-7.15 (d, 1H), 7.11 (s, 1H), 6.86-6.82 (m, 2H), 5.91-5.87 (t, 1H), 4.00-3.97 (t, 2H), 3.89 (s, 3H), 3.12-3.08 (q, 2H), 2.10-1.75 (m, 10H), 1.53-1.50 (m, 1H), 0.98 (s, 3H), 0.91 (s, 6H), 0.89 (s, 3H); $^{13}$C NMR (100 MHz, CDCl$_3$) δ 168.56, 168.51, 168.28, 154.06, 133.84, 132.20, 132.08, 128.52, 123.15, 122.20, 111.96, 111.28, 100.43, 88.29, 86.84, 80.28, 55.73, 41.96, 40.37, 38.24, 24.81, 24.62, 24.48, 24.46, 24.42, 22.74, 22.32, 20.79 ppm. HRMS (m/z): calculated for C$_{33}$H$_{41}$N$_2$O$_9$ [M+H]$^+$ 609.2807; found 609.2809.

Compound 9

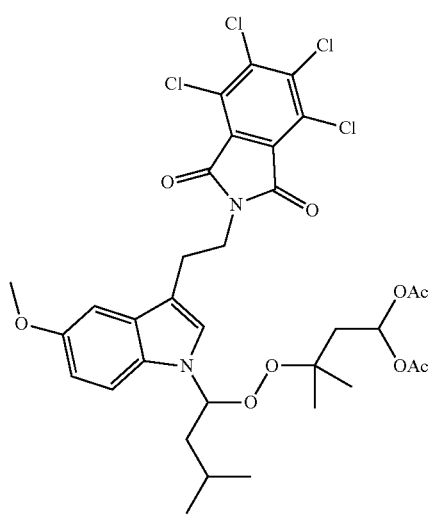

Compound 9 was obtained using a similar procedure as used for Compound 7. A 0.6 mmol scale based on the indole was used and a colorless solid product (313 mg) was obtained, 70% yield. Hexane:EtOAc 3:1. $^1$H NMR (400 MHz, CDCl$_3$) δ 7.37-7.49 (d, 1H), 7.11 (s, 1H), 7.09-7.08 (d, 1H), 6.86-6.83 (q, 2H), 5.91-5.88 (t, 1H), 4.01-3.97 (q, 2H), 3.88 (s, 3H), 3.12-3.08 (q, 2H), 2.11-1.75 (m, 10H), 1.57-1.53 (m, 1H), 1.00-0.97 (m, 12H); $^{13}$C NMR (100 MHz, CDCl$_3$) δ 169.40, 168.54, 168.49, 163.46, 154.14, 139.95, 132.00, 129.52, 128.47, 127.68, 123.38, 112.17, 111.37, 100.36, 112.17, 111.37, 100.36, 89.33, 88.28, 86.95, 80.34, 80.31, 55.78, 42.00, 40.87, 40.47, 39.19, 24.83, 24.68, 24.55, 24.42, 24.09, 22.73, 22.36, 20.88, 20.79 ppm. HRMS (m/z): calculated for C$_{33}$H$_{37}$Cl$_{14}$N$_2$O$_9$ [M+H]$^+$ 745.1248; found 745.1249.

Compound 10

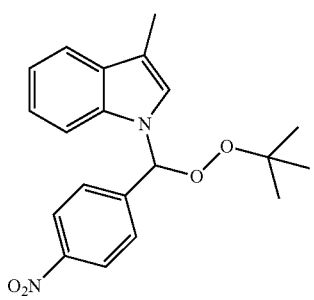

Compound 10 was obtained using a similar procedure as used for Compound 1, except a longer reaction time of 2 hours was used. The product was obtained as a colorless crystal solid (248 mg, 70% yield), Hexane:EtOAc 20:1. $^1$H NMR (500 MHz, CDCl$_3$) δ 8.23-8.22 (d, J=5 Hz, 2H), 7.60-7.58 (d, J=10 Hz, 1H), 7.53-7.52 (d, J=5 Hz, 2H), 7.32-7.30 (d, J=10 Hz, 1H), 7.21-7.16 (m, 2H), 7.04 (s, 1H), 6.84 (s, 1H), 2.32 (s, 3H), 1.15 (s, 9H); $^{13}$C NMR (125 MHz, CDCl$_3$) δ 148.15, 143.26, 136.81, 129.69, 127.81, 123.69, 123.54, 122.11, 119.86, 119.18, 112.81, 110.37, 87.34, 81.73, 26.43, 26.22, 9.63 ppm. HRMS (m/z): calculated for C$_{20}$H$_{23}$N$_2$O$_4$ [M+H]$^+$ 355.1652; found 355.1655.

Compound 11

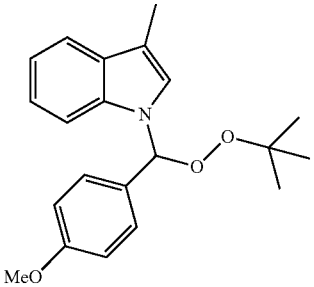

Compound 11 was obtained using a similar procedure as used for Compound 1, except a longer reaction time of 2 hours was used. The product was obtained as a colorless crystal solid (67 mg, 20% yield), Hexane:EtOAc 3:1. $^1$H NMR (600 MHz, CDCl$_3$) δ 7.57-7.56 (d, J=7.8 Hz, 1H), 7.37-7.36 (d, J=8.0 Hz, 1H), 7.24-7.23 (d, J=8.0 Hz, 2H), 7.18-7.12 (m, 2H), 6.98 (s, 1H), 6.95 (s, 1H), 6.88-6.87 (d, J=8.0 Hz, 2H), 3.81 (s, 3H), 2.32 (s, 3H), 1.16 (s, 3H); $^{13}$C NMR (150 MHz, CDCl$_3$) δ 159.83, 136.91, 129.49, 128.38, 128.00, 123.70, 121.55, 119.23, 118.85, 113.81, 111.69, 110.62, 88.23, 81.19, 55.26, 26.30, 9.75 ppm. HRMS (m/z): calculated for C$_{21}$H$_{26}$NO$_3$ [M+H]$^+$ 340.1907; found 340.1911.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus, a combination of steps, elements, components, or constituents can be explicitly mentioned herein; however, all other combinations of steps, elements, components, and constituents are included, even though not explicitly stated.

What is claimed is:

1. A compound of the following formula:

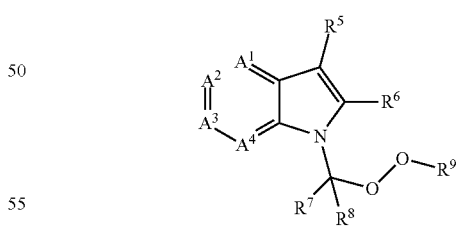

or a pharmaceutically acceptable salt or prodrug thereof, wherein:

A$^1$, A$^2$, A$^3$, and A$^4$ are each independently selected from CR and N, wherein each R is selected from the group consisting of hydrogen, halogen, cyano, trifluoromethyl, alkoxy, aryloxy, substituted or unsubstituted carbonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl;

$R^5$ and $R^6$ are each independently selected from hydrogen, halogen, cyano, trifluoromethyl, alkoxy, aryloxy, substituted or unsubstituted carbonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and $R^7$, $R^8$, and $R^9$ are each independently selected from hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl;

wherein $R^5$ and $R^6$ do not combine to form a cyclic compound.

2. The compound of claim 1, wherein the compound has the following formula:

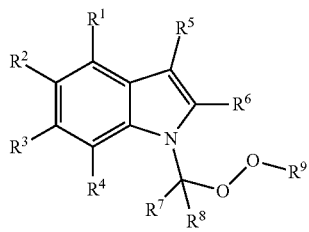

or a pharmaceutically acceptable salt or prodrug thereof, wherein:

$R^1$, $R^2$, $R^3$, $R^4$, $R^5$, and $R^6$ are each independently selected from hydrogen, halogen, cyano, trifluoromethyl, alkoxy, aryloxy, substituted or unsubstituted carbonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and $R^7$, $R^8$, and $R^9$ are each independently selected from hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl;

wherein $R^5$ and $R^6$ do not combine to form a cyclic compound.

3. The compound of claim 2, wherein at least one of $R^1$, $R^3$, $R^4$, $R^6$, and $R^8$ is hydrogen.

4. The compound of claim 2, wherein $R^2$ is hydrogen or alkoxy.

5. The compound of claim 2, wherein $R^5$ or $R^9$ or $R^7$ is substituted or unsubstituted alkyl.

6. The compound of claim 2, wherein $R^7$ is substituted or unsubstituted aryl.

7. The compound of claim 2, wherein the compound has the following formula:

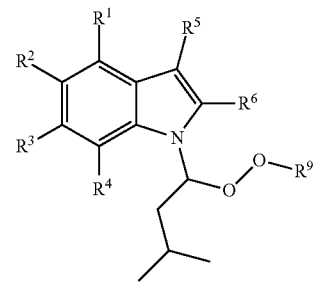

or a pharmaceutically acceptable salt or prodrug thereof.

8. The compound of claim 7, wherein the compound is selected from the group consisting of:

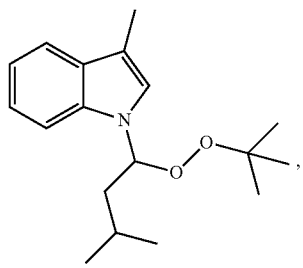

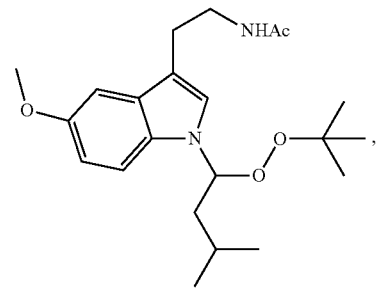

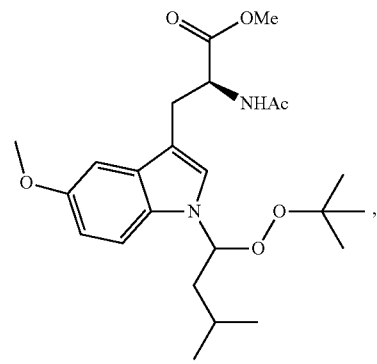

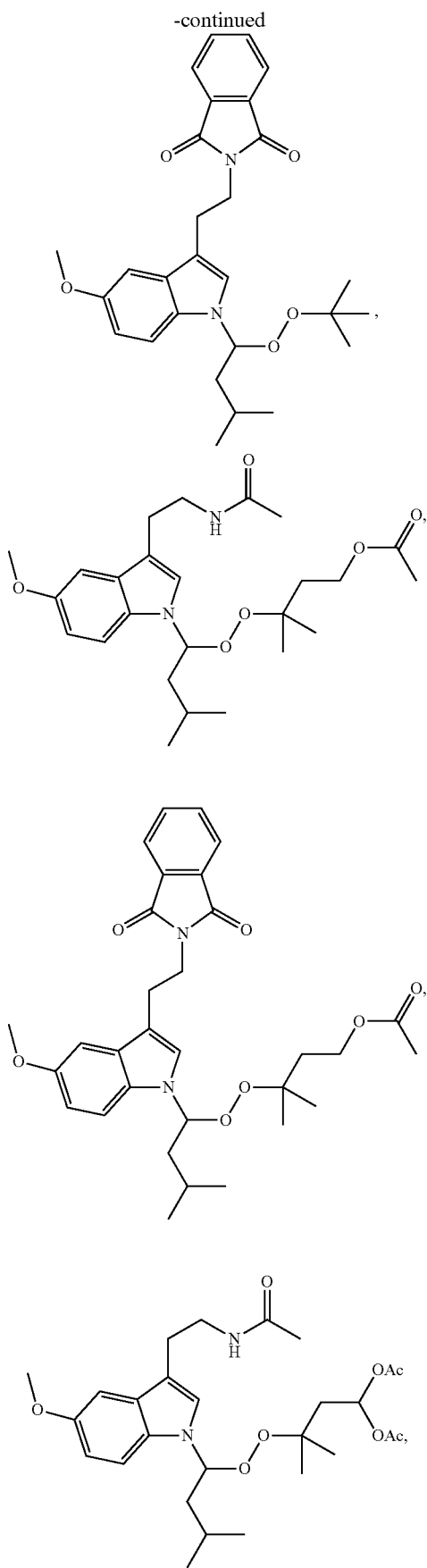
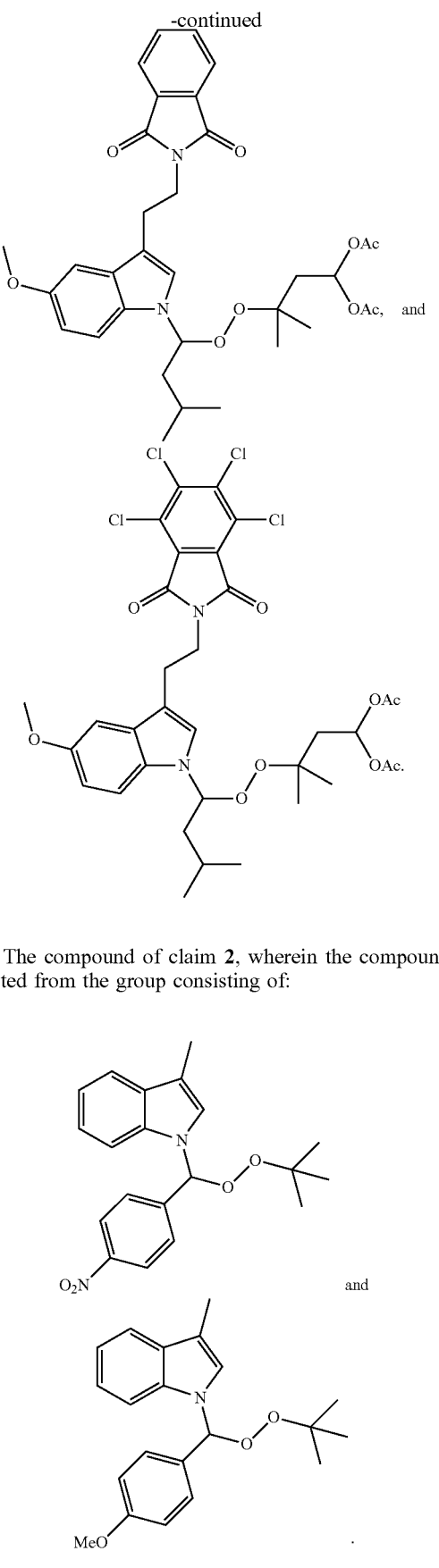
9. The compound of claim 2, wherein the compound is selected from the group consisting of:
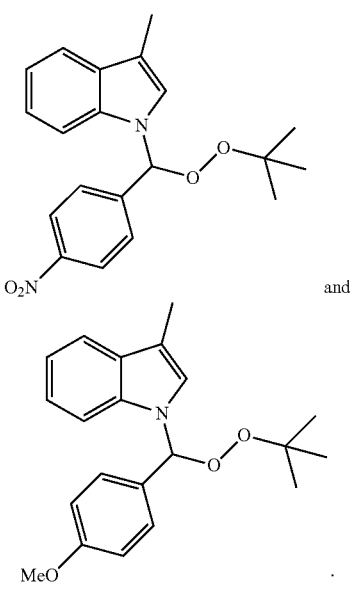

10. A composition comprising a compound of claim 1 and a pharmaceutically acceptable carrier.

11. The compound of claim 2, wherein the compound has the following formula:

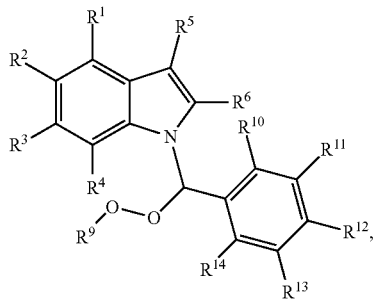

or a pharmaceutically acceptable salt or prodrug thereof, wherein:
$R^{10}$, $R^{11}$, $R^{12}$, $R^{13}$ and $R^{14}$ are each independently selected from hydrogen, halogen, cyano, trifluoromethyl, alkoxy, substituted or unsubstituted carbonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

12. A method of treating a parasitic infection, comprising: administering to a subject in need thereof an effective amount of a compound having the structure:

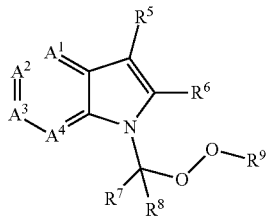

or a pharmaceutically acceptable salt or prodrug thereof, wherein:
$A^1$, $A^2$, $A^3$, and $A^4$ are each independently selected from CR and N, wherein each R is selected from the group consisting of hydrogen, halogen, cyano, trifluoromethyl, alkoxy, aryloxy, substituted or unsubstituted carbonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl;
$R^5$ and $R^6$ are each independently selected from hydrogen, halogen, cyano, trifluoromethyl, alkoxy, aryloxy, substituted or unsubstituted carbonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and
$R^7$, $R^8$, and $R^9$ are each independently selected from hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl;
wherein $R^5$ and $R^6$ do not combine to form a cyclic compound.

13. The method of claim 12, wherein the parasitic infection is a *Plasmodium* infection.

14. The method of claim 13, wherein the *Plasmodium* infection is a *Plasmodium falciparum* infection.

15. The method of claim 12, wherein the parasitic infection is malaria.

16. The method of claim 12, further comprising administering to the subject an antimalarial agent.

17. A method of treating a bacterial infection in a subject, comprising: administering to a subject in need thereof an effective amount of a compound having the structure:

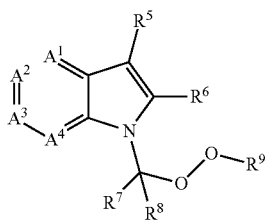

or a pharmaceutically acceptable salt or prodrug thereof, wherein:
$A^1$, $A^2$, $A^3$, and $A^4$ are each independently selected from CR and N, wherein each R is selected from the group consisting of hydrogen, halogen, cyano, trifluoromethyl, alkoxy, aryloxy, substituted or unsubstituted carbonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl;
$R^5$ and $R^6$ are each independently selected from hydrogen, halogen, cyano, trifluoromethyl, alkoxy, aryloxy, substituted or unsubstituted carbonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and R⁷, R⁸, and R⁹ are each independently selected from hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl;

wherein R⁵ and R⁶ do not combine to form a cyclic compound.

18. The method of claim 17, further comprising administering to the subject an antibacterial agent.

19. A method of treating cancer in a subject, comprising: administering to a subject in need thereof an effective amount of a compound having the structure:

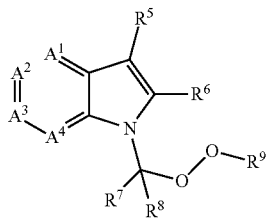

or a pharmaceutically acceptable salt or prodrug thereof, wherein:

A¹, A², A³, and A⁴ are each independently selected from CR and N, wherein each R is selected from the group consisting of hydrogen, halogen, cyano, trifluoromethyl, alkoxy, aryloxy, substituted or unsubstituted carbonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl;

R⁵ and R⁶ are each independently selected from hydrogen, halogen, cyano, trifluoromethyl, alkoxy, aryloxy, substituted or unsubstituted carbonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and R⁷, R⁸, and R⁹ are each independently selected from hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl;

wherein R⁵ and R⁶ do not combine to form a cyclic compound;

wherein the cancer is selected from the group consisting of bladder cancer, brain cancer, breast cancer, colorectal cancer, colon cancer, rectal cancer, cervical cancer, chondrosarcoma, endometrial cancer, gastrointestinal cancer, gastric cancer, genitourinary cancer, head and neck cancer, hepatocellular carcinoma, liver cancer, lung cancer, ovarian cancer, pancreatic cancer, prostate cancer, renal cancer, skin cancer, and testicular cancer.

20. The method of claim 19, further comprising administering to the subject an anticancer agent.

* * * * *